（12） United States Patent
Matsumoto (10) Patent No.: US 7,216,979 B2
(45) Date of Patent: May 15, 2007

(54) OPHTHALMOLOGIC IMAGE PICKUP APPARATUS

(75) Inventor: Kazuhiro Matsumoto, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 727 days.

(21) Appl. No.: 10/459,940

(22) Filed: Jun. 12, 2003

(65) Prior Publication Data

US 2003/0231242 A1   Dec. 18, 2003

(30) Foreign Application Priority Data

Jun. 17, 2002   (JP) .............................. 2002-175805

(51) Int. Cl.
*A61B 3/10*   (2006.01)

(52) U.S. Cl. ...................... 351/205; 351/206

(58) Field of Classification Search ................ 382/254, 382/255, 274, 275; 351/200, 205, 206, 221, 351/246

See application file for complete search history.

(56) References Cited

U.S. PATENT DOCUMENTS

| 3,851,954 | A |   | 12/1974 | Kato et al. | |
|---|---|---|---|---|---|
| 4,102,563 | A |   | 7/1978 | Matsumura et al. | |
| 5,153,926 | A | * | 10/1992 | Jansson et al. | 382/128 |
| 5,268,771 | A | * | 12/1993 | Murakami et al. | 358/448 |
| 5,530,494 | A |   | 6/1996 | Ogawa et al. | |
| 5,828,451 | A | * | 10/1998 | Bellus et al. | 356/326 |
| 6,361,167 | B1 | * | 3/2002 | Su et al. | 351/206 |
| 6,477,282 | B1 | * | 11/2002 | Ohtsuki et al. | 382/266 |
| 7,006,708 | B1 | * | 2/2006 | Nako et al. | 382/294 |
| 2001/0028438 | A1 |   | 10/2001 | Matsumoto | 351/206 |
| 2003/0086624 | A1 | * | 5/2003 | Garcia | 382/275 |
| 2003/0142753 | A1 | * | 7/2003 | Gunday | 375/240.29 |

FOREIGN PATENT DOCUMENTS

EP   1 138 256 A2   4/2001
KR   1999-0075162   10/1999

OTHER PUBLICATIONS

European Search Report, dated Sep. 11, 2003.

* cited by examiner

*Primary Examiner*—Huy Mai
(74) *Attorney, Agent, or Firm*—Morgan & Finnegan LLP (57) ABSTRACT

There is provided an ophthalmologic image pickup apparatus in which a pattern of an image resulting from unnecessary reflected light generated in an optical system by illumination of an illumination unit is stored in a storage unit and the image resulting from the unnecessary reflected light is eliminated using a correction pattern in accordance with an image pickup condition.

10 Claims, 9 Drawing Sheets

OPHTHALMOLOGIC IMAGE PICKUP APPARATUS

BACKGROUND OF THE INVENTION

1. Field of the Invention

The present invention relates to an ophthalmologic image pickup apparatus used in an ophthalmologic doctor's office and the like.

2. Related Background Art

Up to now, according to an eye fundus camera, the illumination and the image pickup of an eye fundus are conducted using a common objective lens. Among illumination light, reflected light from the surface of the objective lens, a smudge or a scratch on its surface, a bubble in the lens, etc, is directly incident into an image pickup optical system as ghost light and overlapped with an eye fundus image. Therefore, the reflected light becomes a cause in which a ghost image is generated. In order to suppress the generation of the ghost light, a strict standard is applied to an appearance concerning, for example, a bubble in the lens and a scratch on its surface; an antireflective film to which a strict specification is applied is used; and a black spot is provided in an illumination optical system.

Also, with respect to ghost light resulting from parts except the object lens, in order to suppress the generation of such light, the selection and special processing of parts, the limitation on design, postprocessing to the optical systems, and the like are conducted.

However, in the above-mentioned conventional example, even if a black spot is provided on an optical path, there is no effect using the black spot with respect to light diffused in an optical member between the black spot and the objective lens. Accordingly, there is a problem that it is difficult to completely eliminate the ghost light. Therefore, a standard required to the objective lens and the like becomes stricter, so that a part cost becomes higher or it takes much time for adjustment and assembly operations. Thus, there is a problem that a remarkable increase in assembly cost is caused.

SUMMARY OF THE INVENTION

An object of the present invention is to solve the above-mentioned problems and to provide an ophthalmologic image pickup apparatus in which ghost light generated in optical systems can be eliminated to improve an image quality.

In order to achieve the above-mentioned object, the present invention provides an ophthalmologic image pickup apparatus including:

image pickup means for picking up an image of an eye to be examined;

illumination means for illuminating the eye to be examined;

storage means for storing a correction pattern for correcting a reflected image resulting from ghost light generated in an image pickup optical system during illumination by the illumination means;

detection means for detecting an image pickup condition; and correction means for correcting the picked up image using the correction pattern stored in the storage means in accordance with a detection output of the detection means.

DESCRIPTION OF THE PREFERRED EMBODIMENTS

Hereinafter, the present invention will be described in detail with reference to embodiments shown in the drawings.

First Embodiment

Figure 1:
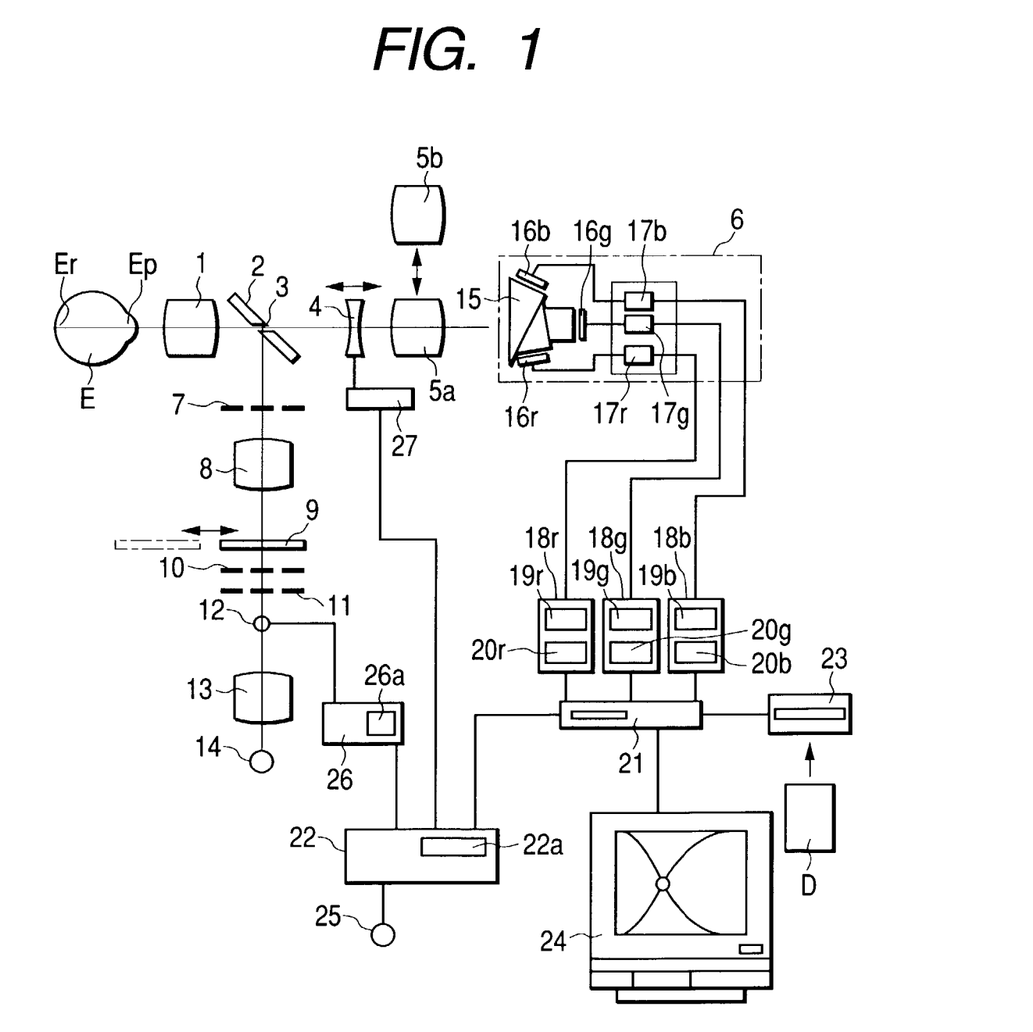
FIG. 1 is a structural view of an eye fundus camera of a first embodiment.

FIG. 1 is a structural view of an eye fundus camera in which the present invention is embodied. In front of an eye to be examined E, an objective lens 1, a holed mirror 2, an image pickup diaphragm 3 located in a hole of the holed mirror 2, a focal lens 4, image pickup lenses 5a and 5b with which a magnification can be changed by exchange thereof, and an image pickup mechanism 6 are disposed.

In an eye fundus illumination system which is located in a light incident direction of the holed mirror 2, a cornea diaphragm 7 which is a diaphragm having a ring-shaped opening for a ring pattern to be projected near a cornea, a relay lens 8, an infrared light cutting filter 9 which is insertable onto an optical path and cuts infrared light, a crystalline lens diaphragm 10 which is a diaphragm having a ring-shaped opening for a ring pattern to be projected near the posterior crystalline lens of the eye to be examined E, a ring diaphragm 11 which is a diaphragm having a ring-shaped opening for a ring pattern to be projected near the pupil of the eye to be examined E, an image pickup light source 12 composed of a stroboscopic tube, a condenser lens 13, and an observation light source 14 such as a halogen lamp for emitting stationary light are disposed from the holed mirror 2 side.

The image pickup mechanism 6 is composed of a color separation prism 15, image pickup elements 16r, 16g, and 16b. Respective outputs of the image pickup elements 16r, 16g, and 16b are connected with image boards 18r, 18g, and 18b through signal amplifying circuits 17r, 17g, and 17b.

The image boards 18r, 18g, and 18b are composed of A/D converting sections 19r, 19g, and 19b for red, green, and blue signals and image memories 20r, 20g, and 20b. Respective outputs of the image boards 18r, 18g, and 18b are connected with an image control unit 21.

The image control unit 21 is connected with a control unit 22, an image recording unit 23, and a television monitor 24.

The image recording unit 23 is regarded as a drive device for conducting writing into and readout from a nonvolatile recording medium D such as an MO, an MD, a DVD-RAM, a VTR tape, or a hard disk.

The control unit 22 is connected with an image pickup switch 25 and a focal lens position detecting unit 27 for detecting the position of the focal lens 4 and also connected with the image pickup light source 12 through a stroboscopic light emission control circuit 26. The control unit 22 includes a memory 22a. The stroboscopic light emission control circuit 26 includes a capacitor 26a for controlling the amount of light to be emitted.

When an image of a fundus Er of the eye to be examined E is picked up using such an eye fundus camera, a person to be examined is seated in the front of a person who picks up the image. Then, while observing the fundus Er of the eye to be examined E with infrared light, the person picking up the image conducts the alignment between the eye to be examined E and the eye fundus camera. In addition, when low magnification image pickup is selected by a magnification changing switch not shown, the image pickup lens 5a for low magnification is disposed on the optical path. When enlarging image pickup is selected, the image pickup lens 5b for enlargement is disposed on the optical path. With this observation state, the infrared light cutting filter 9 is removed from the optical path.

Infrared light emitted from the observation light source 14 in observation is condensed by the condenser lens 13, passes through the image pickup light source 12, the opening of the diaphragm 11, the lens 8, and the opening of the cornea diaphragm 7, and is reflected toward the left in the drawing by a mirror portion in the vicinity of the hole of the holed mirror 2. The reflected light passes through the objective lens 1 and an eye pupil Ep to illuminate the eye fundus Er. An image of the eye fundus Er illuminated with the infrared light is again passed through the objective lens 1, the image pickup diaphragm 3, the focal lens 4, and the image pickup lens 5a (5b) and incident into the color separation prism 15 of the image pickup mechanism 6.

The color separation prism 15 guides the infrared light and red light to the image pickup element 16r, guides blue light to the image pickup element 16b, and guides green light to the image pickup element 16g. Because observation light is infrared light, it is imaged onto the image pickup element 16r and converted into an electrical signal. This signal is amplified by the signal amplifying circuit 17r by a gain predetermined for observation and inputted to the image control unit 21. An image corresponding to the signal is displayed on the television monitor 24.

The person picking up the image, which has observed the image to ensure the completion of the image pickup preparation, operates the image pickup switch 25. The control unit 22 which has detected the input by the image pickup switch 25 causes the infrared light cutting filter 9 to insert onto the optical path and controls the stroboscopic light emission control circuit 26 to discharge the capacitor 26a, thereby emitting light from the image pickup light source 12. The light emitted from the image pickup light source 12 passes through the ring-shaped opening of the diaphragm 11 and the ring-shaped opening of the diaphragm 10. Only visible light of the light transmits through the infrared light cutting filter 9, passes through the relay lens 8, and is reflected toward the left in the drawing by the mirror portion in the vicinity of the hole of the holed mirror 2. The reflected light passes through the objective lens 1 and the eye pupil Ep to illuminate the eye fundus Er.

An image of the eye fundus Er illuminated thus is again passed through the objective lens 1, the image pickup diaphragm 3, the focal lens 4, and the image pickup lens 5a (5b) and incident into the color separation prism 15 to be divided into respective colors. The respective color images are imaged onto the image pickup elements 16r, 16g, and 16b and converted into electrical signals. These signals are amplified by the signal amplifying circuits 17r, 17g, and 17b by predetermined gains, converted into digital image data by the A/D converting sections 19r, 19g, and 19b, and temporally stored in the image memories 20r, 20g, and 20b. Simultaneously, the focal lens position detecting unit 27 detects the position of the focal lens 4 in an image pickup operation and writes the detected position information into the memory 22a of the control unit 22. A correction pattern image as a pattern image resulting from internal reflection of the illumination optical system or the image pickup optical system according to the position of the focal lens 4 is stored for each of colors of R (red), G (green), and B (blue) in the memory 22a.

Figure 2A:
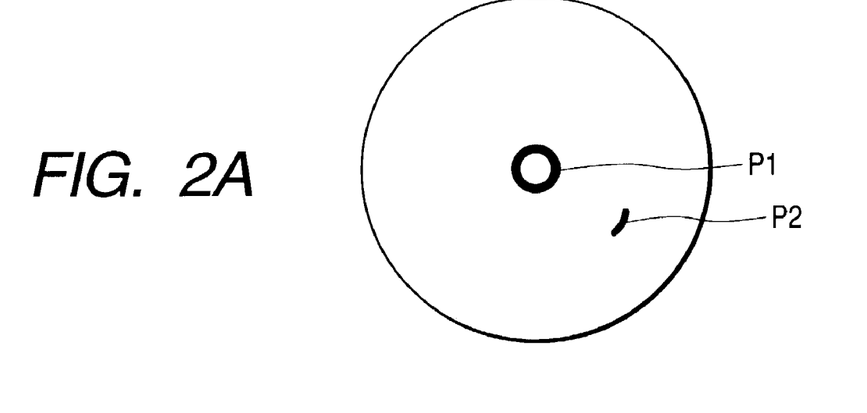
FIGS. 2A, 2B and 2C are explanatory views of a correction pattern image.
Figure 2B:
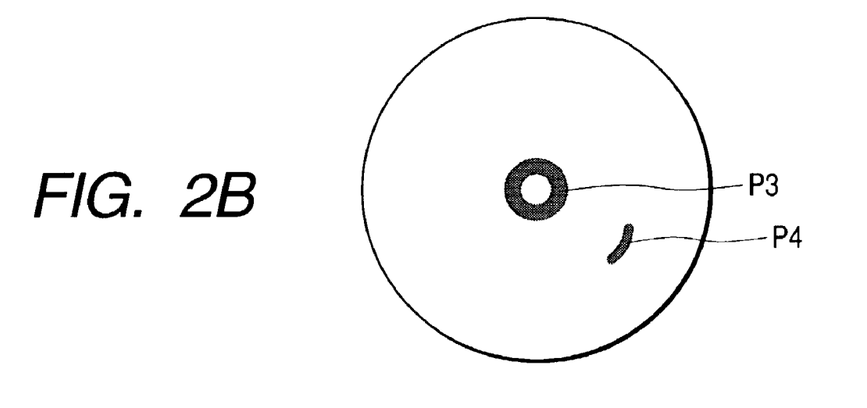
Figure 2C:
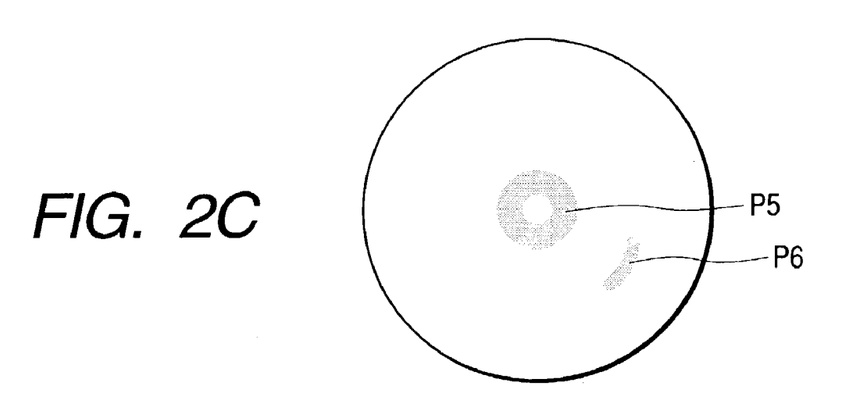

FIG. 2A shows a G-image of the correction pattern image corresponding to, for example, −12D (diopter). There is a reflected image P1 of the objective lens 1 in the central region of the image and there is a reflected image P2 resulting from a scratch, a bubble, a smudge, or the like of the object lens 1 in the peripheral region thereof. FIG. 2B shows a G-image of the correction pattern image corresponding to, for example, −6D (diopter). Contrasts of reflected images P3 and P4 become lower than those of the reflected images P1 and P2 because of a difference of image pickup diopters. FIG. 2C shows a G-image of the correction pattern image corresponding to, for example, 0D. Contrasts of reflected images P5 and P6 are still lower than those of the reflected images P3 and P4 and the areas thereof are expanded.

The control unit 22 produces an image used for correction which corresponds to an actual image pickup condition based on the detected dioptric information and the stored correction pattern image.

When the detected dioptric information is given by Dk(D) and it is assumed that the correction pattern images of Dm(D) and Dn(D) (Dm<Dk<Dn) are stored, image data Kr(Dk, i, j), Kg(Dk, i, j), and Kb(Dk, i, j) of a correction pattern image at an address (i, j) thereof can be calculated from the following equations.

$$Kr(Dk,i,j)=\{Kr(Dm,i,j)\cdot(Dm-Dk)+Kr(Dn,i,j)\cdot(Dn-Dk)\}/(Dn-Dm)$$

$$Kg(Dk,i,j)=\{Kg(Dm,i,j)\cdot(Dm-Dk)+Kg(Dn,i,j)\cdot(Dn-Dk)\}/(Dn-Dm)$$

$$Kb(Dk,i,j)=\{Kb(Dm,i,j)\cdot(Dm-Dk)+Kb(Dn,i,j)\cdot(Dn-Dk)\}/(Dn-Dm)$$

Because a γ characteristic of a television camera is added to the thus obtained correction pattern image, reverse correction of γ is performed. When corrected image data after the reverse correction are given by Kr' (Dk, i, j), Kg' (Dk, i, j), and Kb' (Dk, i, j) and the image is assumed as an 8-bit image, a maximum value of the image becomes a value of up to 255. Further, when γ=0.45 in a television camera used for image pickup, the following equations are obtained.

$$Kr'(Dk,i,j)=255\cdot\{Kr(Dk,i,j)/255\}^{(1/0.45)}$$

$$Kg'(Dk,i,j)=255\cdot\{Kg(Dk,i,j)/255\}^{(1/0.45)}$$

$$Kb'(Dk,i,j)=255\cdot\{Kb(Dk,i,j)/255\}^{(1/0.45)}$$

Also, when an illumination light intensity in the image pickup of the correction pattern image is given by Fo and an illumination light intensity in the image pickup of the eye to be examined E is given by Fk, corrected image data after correction can be calculated as follows.

$$Kr''(Dk,i,j)=Kr'(Dk,i,j)\cdot 2(Fk-Fo)$$

$$Kg''(Dk,i,j)=Kg'(Dk,i,j)\cdot 2(Fk-Fo)$$

$$Kb''(Dk,i,j)=Kb'(Dk,i,j)\cdot 2(Fk-Fo)$$

Next, because the γ correction is performed on the picked up eye fundus image by the television camera, the γ reverse correction is performed. When image data of the picked up eye fundus image at an address (i, j) thereof are given by Fr(i, j), Fg(i, j), and Fb(i, j) and image data after the γ inverse correction are given by Fr'' (i, j), Fg'' (i, j), and Fb'' (i, j), the following equations are obtained.

$$Fr''(i,j)=255\cdot\{(Fr(i,j)/255)\}^{(0.45)}$$

$$Fg''(i,j)=255\cdot\{(Fg(i,j)/255)\}^{(0.45)}$$

$$Fb''(i,j)=255\cdot\{(Fb(i,j)/255)\}^{(0.45)}$$

The correction pattern image is subtracted from these image data and the γ correction is performed again to obtain a corrected eye fundus image. In other words, when eye fundus data after the correction are given by Fcor_r(i, j), Fcor_g(i, j), and Fcor_b(i, j), these data can be expressed as follows.

$$Fcor\_r(i,j)=255\cdot\{(Fr''(i,j)-Kr''(Dk,i,j))/255\}^{(0.45)}$$

$$Fcor\_g(i,j)=255\cdot\{(Fg''(i,j)-Kg''(Dk,i,j))/255\}^{(0.45)}$$

$$Fcor\_b(i,j)=255\cdot\{(Fb''(i,j)-Kb''(Dk,i,j))/255\}^{(0.45)}$$

Figure 3:
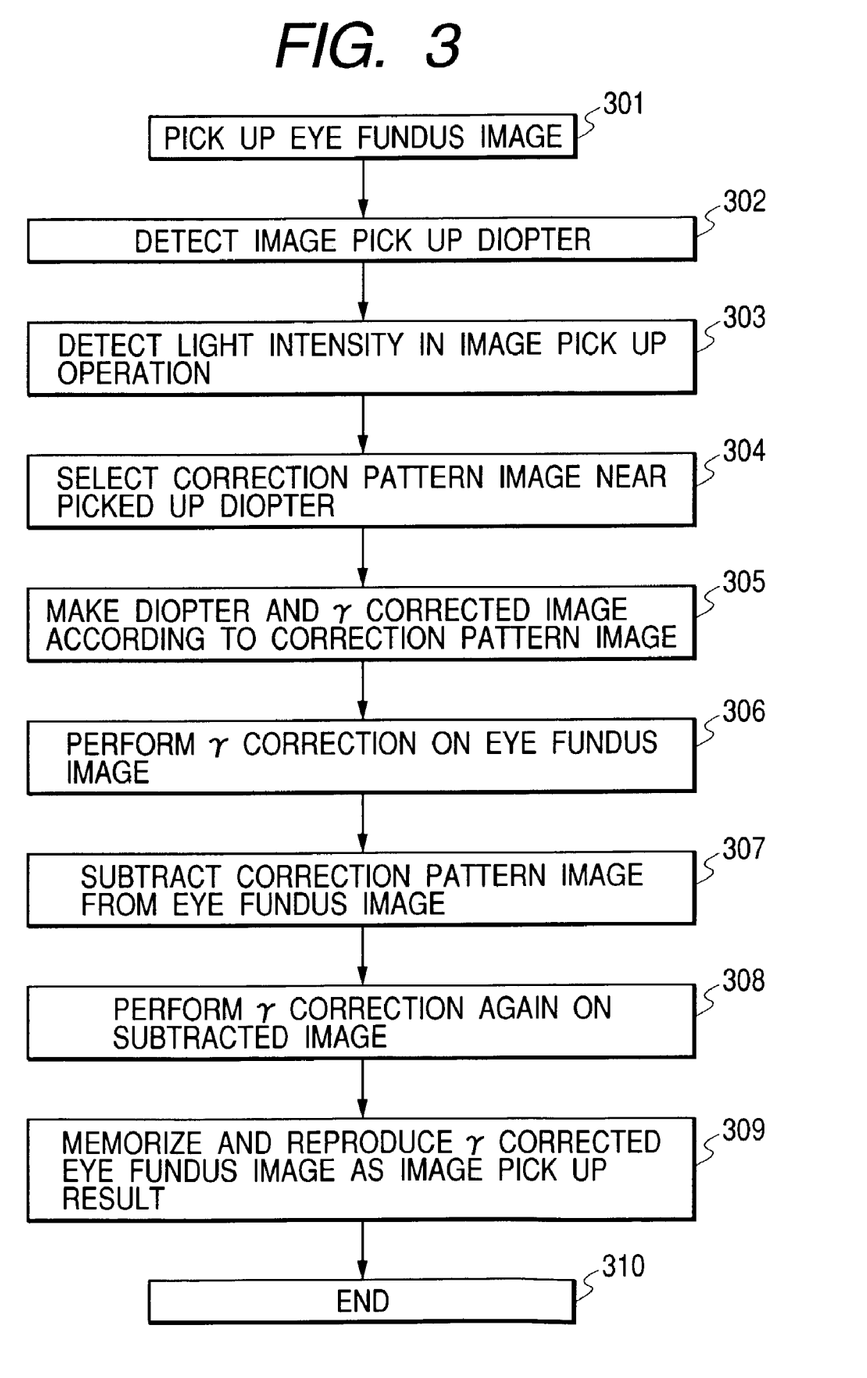
FIG. 3 is a flow chart for correcting a picked up image.

A flow chart shown in FIG. 3 indicates a summary of a flow of such image pickup. It will be described simply.

In step 301, an eye fundus image is picked up. After that, an image pickup diopter is detected in step 302 and a correction pattern image near the detected image pickup diopter is selected in step 304. In step 303, a light intensity in image pickup operation is detected.

After that, in step 305, the selected correction pattern image near the image pickup diopter is further corrected according to the detected diopter and then the γ reverse correction is performed. Further, the correction pattern image is detected in step 303.

In step 306, the γ reverse correction is performed on the picked up eye fundus image. After that, the correction pattern is subtracted from the eye fundus image in step 307 and the γ correction is performed again on a resultant image in step 308. Thus, an accurate eye fundus image in which ghost light is eliminated can be obtained.

In step 309, the accurately γ-corrected eye fundus image can be memorized and reproduced as an image pickup result. In step 310, all operations are completed.

The concept of such an image correcting method is applied to not only the case of low magnification image pickup using the image pickup lens 5a but also the case of enlarging image pickup using the image pickup lens 5b. Here, the respective correction pattern images for low magnification and enlargement may be separately stored. Alternatively, the magnification of the correction pattern image for low magnification or enlargement may be corrected to use the correction pattern image after the correction of magnification. Because there is a probability that the optical axes of the image pickup lenses for low magnification and enlargement are decentered at this time, it is necessary to store the amount of decentering.

Figure 4A:
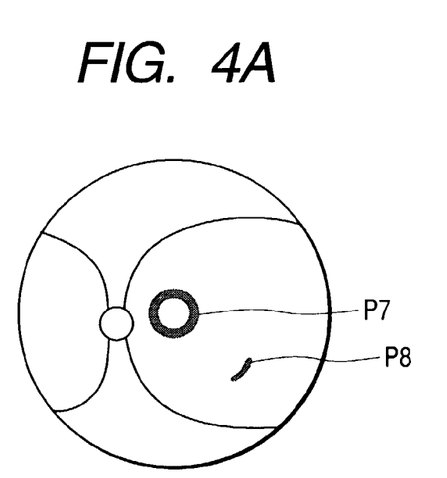
FIGS. 4A and 4B are explanatory views for correction of an eye fundus image.
Figure 4B:
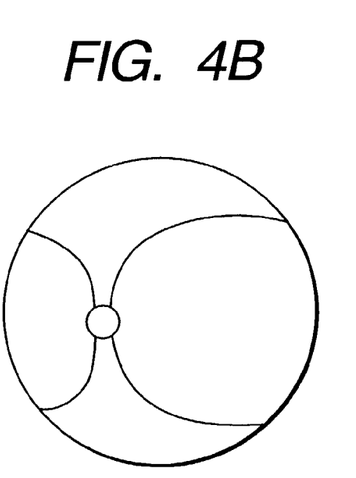

Thus, as shown in FIG. 4A, reflected images P7 and P8 resulting from the reflection of an internal optical system of the eye fundus camera are overlapped on the picked up original image in the central region and the peripheral region thereof. However, according to the above-mentioned calculation, as shown in FIG. 4B, an image in which these reflected images are eliminated can be obtained. The image data is recorded in the recording medium D by the recording unit 23 and displayed on the television monitor 27, thereby completing the image pickup.

In the above-mentioned embodiment, the correction pattern image is prepared in advance. However, an optimum correction pattern image is changed with time according to a change in optical system resulting from a smudge or the like. Accordingly, if the correction pattern image is automatically obtained at a time when a power source is turned on, it becomes possible to perform the correction with higher precision.

Second Embodiment

Figure 5:
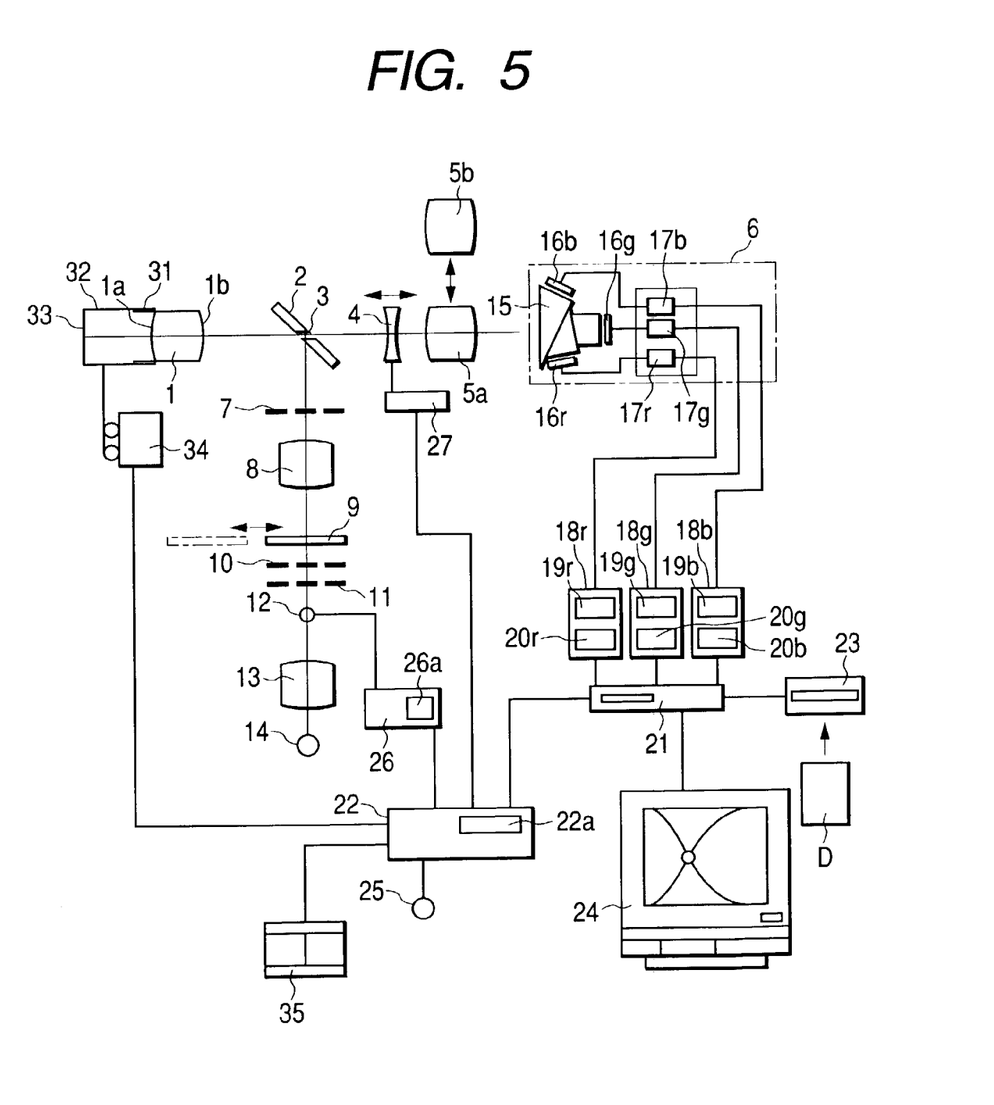
FIG. 5 is a structural view of an eye fundus camera of a second embodiment.

FIG. 5 shows an embodiment for automatically obtaining a correction pattern image at a time when a power source is turned on and the same symbols as those in FIG. 1 indicate the same members. An auxiliary optical member 32 for picking up a correction pattern image is attached to a lens barrel 31 of the objective lens 1. A rear reflecting surface 33 of the auxiliary optical member 32 is composed of a black diffusing surface which hardly reflects light, and disposed in a position substantially conjugate with the image pickup diaphragm 3 with respect to the objective lens 1.

This position substantially corresponds to the pupil position of the eye to be examined E. In the vicinity of the pupil, an image pickup light flux and an illumination light flux are separated from each other. Therefore, there is no case where light reflected on the reflecting surface 33 passes through the image pickup diaphragm 3 and reaches the image pickup elements 16r, 16g, and 16b. The control circuit 22 is connected with a detection switch 34 for detecting whether the auxiliary optical member 32 is attached or not and with a power source switch 35 for instructing that the power source is turned on.

A person picking up an image attaches the auxiliary optical member 32 to the lens barrel 31 of the objective lens 1 and turns on the power source switch 35. After the power source is turned on, when it is detected by the detection switch 34 that the auxiliary optical member 32 is attached, the control unit 22 starts automatic image pickup of a correction pattern image. Because dioptric information for image pickup is stored in the memory 22a, the focal lens 4 is driven for every 1D such as −12, −11, −10, . . . , 0, +1, . . . , +15 according to the dioptric information by a driver unit which is not shown. Then, the stroboscopic image pickup light source 12 emits light. As in the above description, the light emitted from the stroboscopic image pickup light source 12 passes through the ring-shaped opening of the diaphragm 11 and the ring-shaped opening of the diaphragm 10. Then, only visible light of the light transmits through the infrared light cutting filter 9, passes through the relay lens 8, and is reflected toward the left in the drawing by the mirror portion in the vicinity of the hole of the holed mirror 2. The reflected light is reflected on a rear surface 1b and a front surface 1a of the objective lens 1.

A reflected image of the objective lens 1 and an image resulting from a scratch or a smudge on the rear surface 1b or the front surface 1a of the objective lens 1, a bubble in the internal glass of the objective lens 1, or the like, are passed through the image pickup diaphragm 3, the focal lens 4, and the image pickup lens 5a (5b) and incident into the color separation prism 15 to be divided into respective colors. The respective color images are imaged onto the image pickup elements 16r, 16g, and 16b and converted into electrical signals.

These signals are amplified by the signal amplifying circuits 17r, 17g, and 17b by predetermined gains, converted into digital image data by the A/D converting sections 19r, 19g, and 19b, temporally stored in the image memories 20r, 20g, and 20b, and further stored together with dioptric information in the memory 22a of the control unit 22. The control unit 22 repeats image pickup with respect to predetermined diopters to obtain correction pattern images.

The above image pickup may be performed for every time the power source is turned on. However, it takes time until actual image pickup becomes ready after the power source is turned on, so that there is the case where usability is impaired. Therefore, when the control unit 22 has a calendar and a timer which are set such that automatic image pickup of a correction pattern image is performed one time per day or one time per week, the usability is good. In addition, because image pickup is performed immediately after the power source is started up in some cases, when a switch capable of stopping the automatic image pickup is provided, the usability can be further improved. Of course, if necessary, an operation member such as a switch can be provided such that a correction pattern image can be manually picked up.

Figure 6:
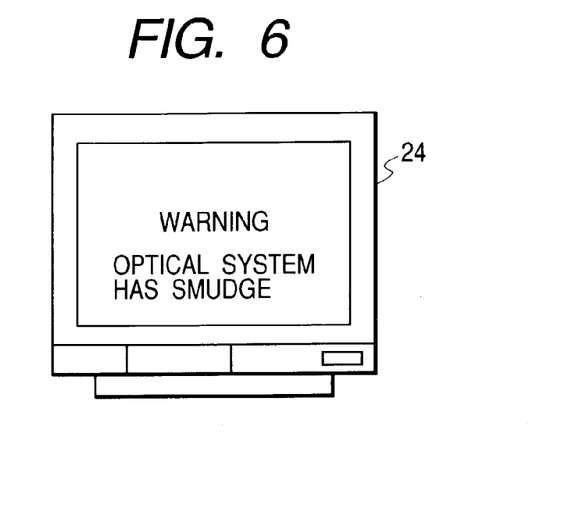
FIG. 6 is an explanatory view of a screen of a television monitor.

Also, the control unit 22 compares a maximum value, an average value, or the like of digitized image data of the correction pattern image with a predetermined value, for example, "32". When the maximum value, the average value, or the like is larger than the predetermined value, as shown in FIG. 6, a warning message is preferably displayed on the television monitor 24 to inform the person picking up the image that an optical system has too much smudge. In other words, this is the case where reflected light is extremely intense. In this case, when a value of the image data of the correction pattern image is added to the eye fundus image data, a resultant value exceeds a maximum value "255" of the image data, so that the correction cannot be performed.

Figure 7:
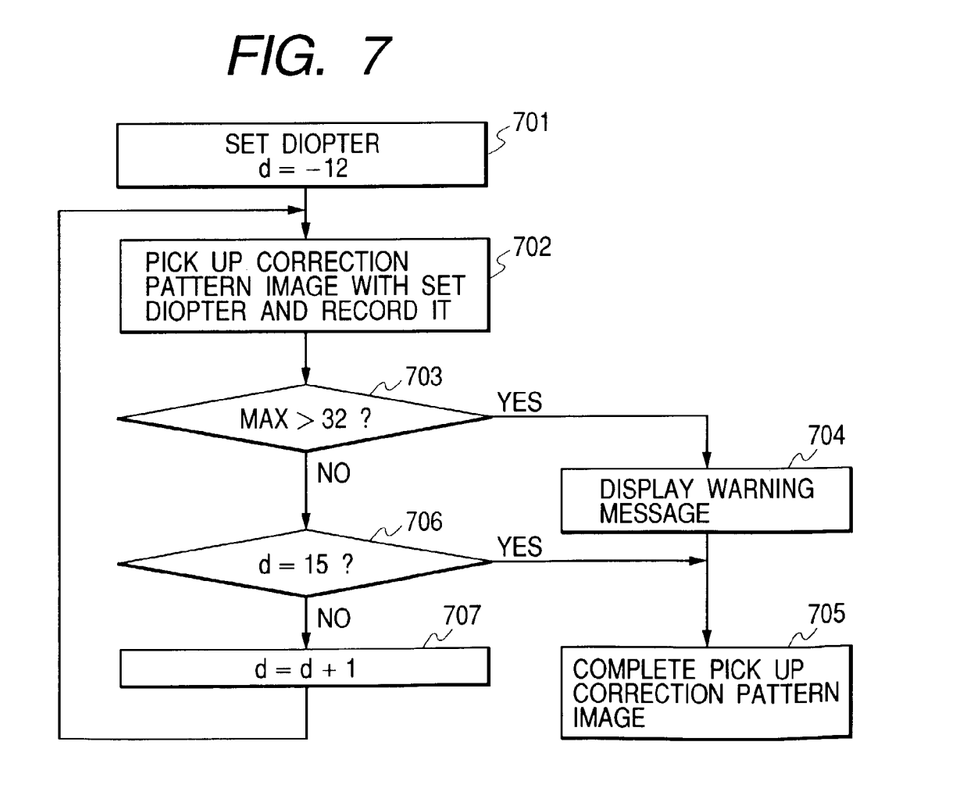
FIG. 7 is a flow chart for correction pattern pickup.

A flow of such processing will be briefly described again with reference to a flow chart shown in FIG. 7.

In step 701, in order to start correction pattern image pickup, the diopter d is set to −12D. In step 702, a correction pattern image is picked up with the set diopter d.

Next, in step 703, it is determined whether or not the average value or the maximum value of the correction pattern image is larger than a predetermined value, for example, 32. When the average value or the maximum value is larger than the predetermined value, that is, when the optical system has too much smudge, processing is transferred to step 705 through step 704 to complete the pickup of the correction pattern image.

When the average value or the maximum value is smaller than the predetermined value "32" for the correction pattern image in step 703, it is determined that the optical system does not have too much smudge and processing is transferred to step 706. In step 706, it is determined whether or not the pickup of the correction pattern image is completed.

When it is completed, the pickup of the correction pattern image is completed in step 705.

On the other hand, when it is not completed, setting is changed to next diopter, processing is returned to step 702 again, and next image pickup is performed.

Also, the auxiliary optical member 32 for picking up the correction pattern image can be formed in a cap of the objective lens 1. It is capped after the image pickup is completed. Therefore, when the power source is turned on next time, a correction pattern image is automatically picked up without fail, so that the optimum correction can be performed at all times.

Further, in the above-mentioned embodiment, the correction pattern image is prepared for each of colors of R, G, and B. However, if the correction pattern image is stored as a luminance signal or a color-difference signal, the same effect is obtained. In addition, in the embodiment, the correction pattern image is stored in the memory 22a and the corrected eye fundus image is recorded in the recording medium D by the recording unit 23. However, recording of the correction pattern image, correction calculation of the image, and storage of the corrected image may be performed using an external PC (personal computer) connected with the eye fundus camera through a network.

Third Embodiment

Figure 8:
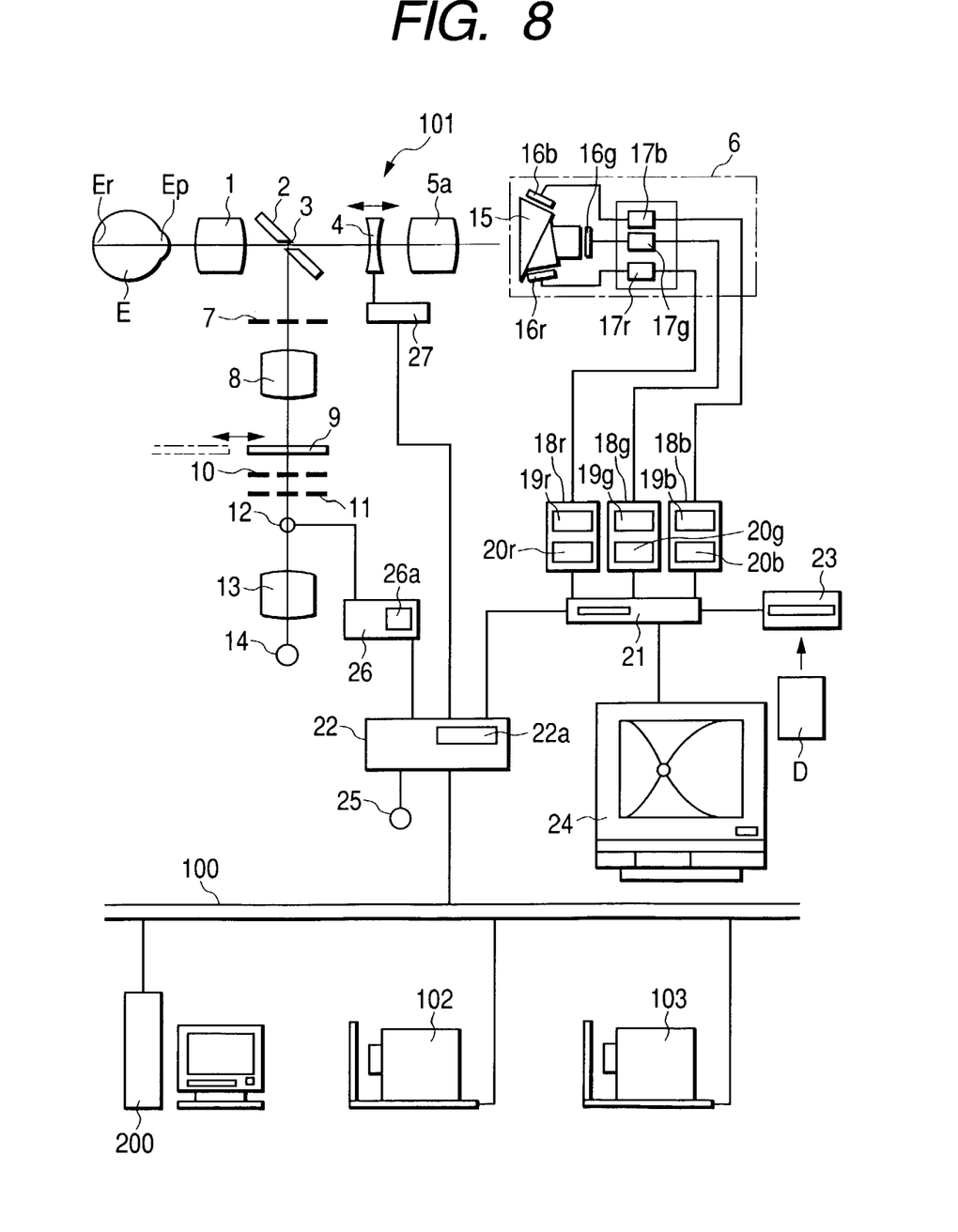
FIG. 8 is a structural view of an eye fundus camera of a third embodiment.

FIG. 8 shows an embodiment in this case. The control unit 22 of an eye fundus camera 101, which has the same structure as in the embodiments described earlier, is connected with a network 100. A picked up image is sent to a computer 200 similarly connected with the network 100. The network 100 is connected with eye fundus cameras 102 and 103 similar to the eye fundus camera 101.

Correction pattern images for the eye fundus cameras 101, 102, and 103 are stored in advance in a memory of the computer 200. An image picked up by the eye fundus camera 101 and an image pickup condition such as an image pickup diopter are sent together with a camera number of the eye fundus camera, for example, "101" to the computer 200 through the network 100. The computer 200 first reads out the correction pattern image from the memory 22a in accordance with the camera number "101" of the eye fundus camera by which image pickup has performed and the image pickup condition. Then, as in the embodiments described earlier, the computer 200 processes the read out correction pattern image according to the image pickup condition and corrects an eye fundus image.

Figure 9:
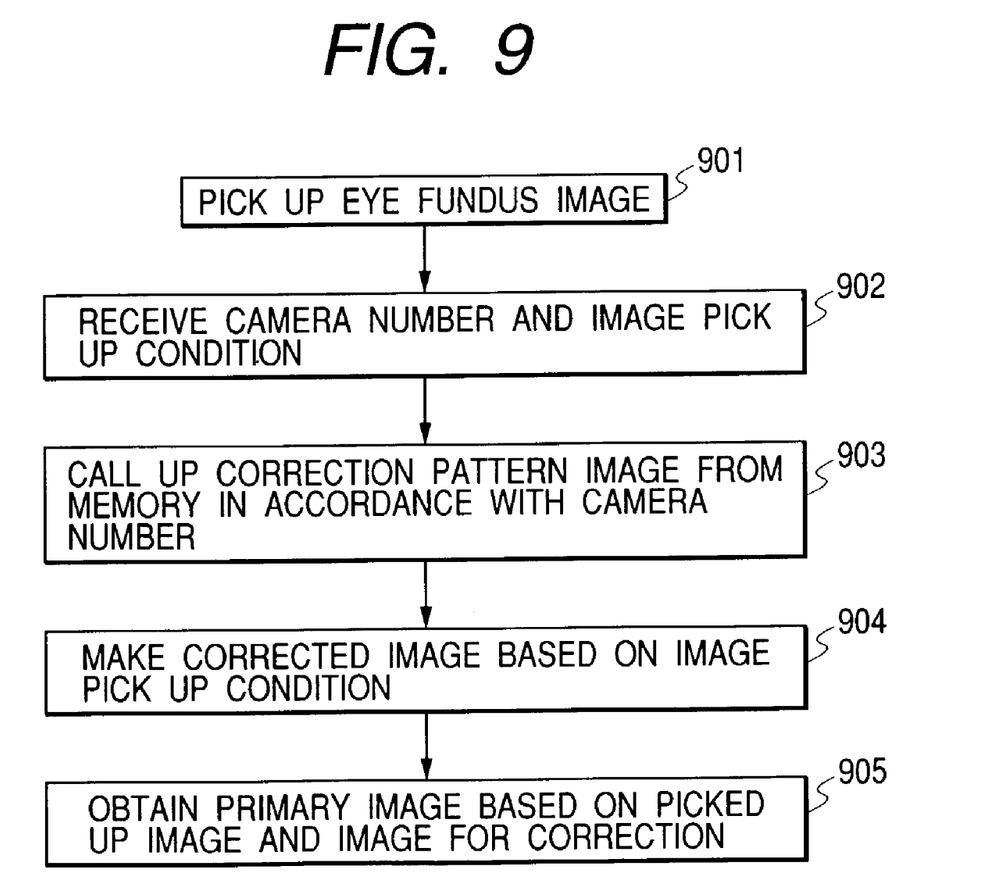
FIG. 9 is a flow chart for an image correction method through a network.

A flow of the above operation will be briefly described with reference to a flow chart shown in FIG. 9.

In step 901, an eye fundus image is picked up by an eye fundus camera connected with the network. After that, the computer connected with the eye fundus camera through the network receives a camera number of the eye fundus camera and an image pickup condition in step 902.

In step 903, the computer calls up a correction pattern image from the memory in accordance with the camera number.

In step 904, the computer makes a corrected image based on the image pickup condition received from the eye fundus camera through the network.

In step 905, the computer obtains an accurate eye fundus image corrected using the picked up eye fundus image and the corrected image.

The detail of the correction is the same as in the first embodiment described earlier.

Similarly, images picked up by the eye fundus cameras 102 and 103 are corrected by the computer 200.

As described above, the correction pattern image is stored in the external computer 200 and the eye fundus image is corrected. Accordingly, as compared with the case where the image is corrected in the main body of the eye fundus camera, the operation speed is high because the performance of the computer 200 is superior. In addition, because a large number of image data can be recorded, high precision correction can be performed in a short time.

Also, in the above-mentioned embodiment, the plurality of correction pattern images are stored. If image pickup can be performed with a state in which a reflected image is focused, an eye fundus image can be corrected from a single correction pattern image. Because a reflected image of the objective lens 1 exists in a range of about −12D to −15D, the reflected image is focused and the correction pattern image is picked up. Because an F number and an exit pupil position in an image pickup system of the eye fundus camera are known, the way in which the image at respective diopter positions is blurred can be obtained by calculation. Thus, the capacity of the memory for storing the correction pattern image can be reduced.

Also, while the optical system of the eye fundus camera is used for a long time, there is the case where dust and the like are entered thereinto, thereby changing the appearance of the reflected image with time to further enhance it. In such a case, it is most preferable to pick up the correction pattern image again at times as described above. When the corrected eye fundus image is checked and it is determined that the correction is insufficient, correction calculation parameter is further changed, so that the high precision correction can be performed.

A region in which the reflected image of the objective lens 1, a scratch or the like is displayed together with the eye fundus image is different from the other region with respect to color. In addition, coordinates of the reflected image, the scratch, and the like are known from the correction pattern image. Therefore, when colors in the above coordinates are compared with those in surrounding addresses and there are different colors, in particular, blue or green is intense, the correction is insufficient. Accordingly, the calculation is performed again, whereby it becomes possible to perform the correction with higher precision. In order to obtain color information at an eye fundus image position corresponding to the position of the reflected image, the correction pattern image according to the image pickup condition is binarized, so that image data of the reflected image region is set to "1" and image data of the other region is set to "0". Then, values of B/G and R/G of the image data are obtained as color information of the reflected image region by AND operation with the eye fundus image. The values are compared with values of B/G and R/G of the eye fundus image data corresponding to a region around the reflected image region. When a difference of these color information is larger than a predetermined value, it is determined that the correction is insufficient.

In that case, preferably, it is assumed that image pickup is performed with an light intensity larger than an actual light intensity in, for example, the above calculation equations, the correction pattern image is corrected, and a resultant image is subtracted from a primary image. In addition, in some cases, when overcorrection is performed so that a corrected region of the image is intense in red, preferably, it is assumed that image pickup is performed with a small light intensity, the correction pattern image is corrected, and the subtraction is performed again. When such operation is repeated, it becomes possible to perform the correction with higher precision.

Figure 10:
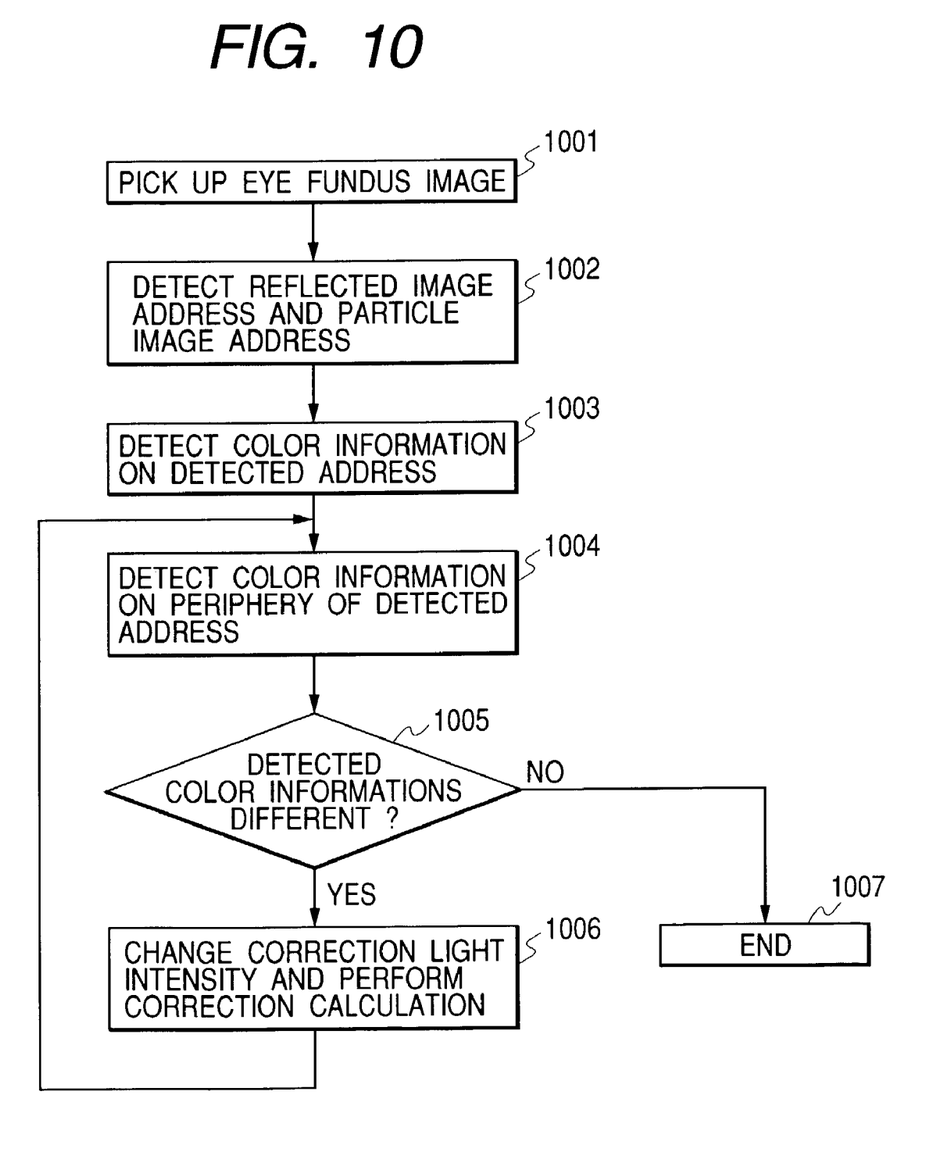
FIG. 10 is a flow chart for a correction method using color information.

This flow will be briefly described with reference to a flow chart shown in FIG. 10.

In step 1001, the eye fundus image is picked up. In step 1002, a reflected image address and a particle image address are detected from the correction pattern image. In step 1003, color information of the eye fundus image at a position corresponding to the detected address is detected.

In step 1004, color information of the image on the periphery of the detected address is detected.

In step 1005, the color information on the detected address is compared with the color information on the periphery thereof. When there is no difference or when the difference is no more than a predetermined value, it is assumed that the correction is finished and the correction operation is completed in step 1007.

On the other hand, when there is the difference, a correction light intensity is changed and the correction calculation is performed again in step 1006.

Processing is returned to step 1004 until the correction is completed and the calculation of an adequate correction value is continued.

As described above, according to the ophthalmologic image pickup apparatus in the present invention, the reflected image resulting from the internal reflection in the illumination optical system and the image pickup optical system is stored in the correction pattern image for each image pickup diopter, the correction pattern image is corrected using the image pickup diopter and the image pickup light intensity, and the corrected image is subtracted from the eye fundus image. Thus, unwanted reflections can be eliminated from the picked up image, so that an image quality can be improved and further the accuracy of diagnosis can be improved.

Also, a yield of parts can be increased and a process time for assembly and adjustment can be shortened, so that a product cost can be reduced to obtain low cost products. Further, when such a correction pattern image is used, there is no case where original image information is lost as compared with a method of processing a primary image to improve an image quality, so that high precision correction can be performed.

What is claimed is:

1. An ophthalmologic image pickup apparatus comprising:
   image pickup means for picking up an image of an eye to be examined;
   illumination means for illuminating the eye to be examined;
   storage means for storing a correction pattern for correcting a reflected image resulting from ghost light generated in an image pickup optical system during illumination by the illumination means;
   detection means for detecting an image pickup condition; and
   correction means for correcting the picked up image, wherein
   the image of the eye to be examined is corrected by the correction means using the correction pattern stored in the storage means and the correction pattern is in accordance with a detection output of the detection means.

2. An ophthalmologic image pickup apparatus according to claim 1, wherein the image pickup condition includes at least one selected from the group consisting of image pickup light intensity information, dioptric information, and image pickup magnification information through the illumination means.

3. An ophthalmologic image pickup apparatus according to claim 1, wherein the storage means has a plurality of correction patterns, and the picked up image is corrected using the correction pattern selected from the plurality of correction patterns in accordance with a detection result of the detection means.

4. An ophthalmologic image pickup apparatus according to claim 1, wherein the picked up image is corrected by calculation from the stored correction pattern in accordance with the detection output of the detection means.

5. An ophthalmologic image pickup apparatus according to claim 1, wherein the correction pattern is obtained at a time of turning on of a power source, at a predetermined time, or at a time of operating a predetermined operation member and stored in the storage means.

6. An ophthalmologic image pickup apparatus according to claim 1, wherein the correction pattern is stored in the storage means connected with an external computer connected with a network.

7. An ophthalmologic image pickup apparatus according to claim 1, wherein the correction means includes an external computer connected with a network.

8. An ophthalmologic image pickup apparatus according to claim 1, wherein the image pickup optical system and the illumination means include a common optical system and the ghost light is generated in the common optical system.

9. An ophthalmologic image pickup apparatus according to claim 8, wherein the common optical system includes an objective lens.

10. An ophthalmologic image pickup apparatus comprising:
   an image pickup device for picking up an image of an eye to be examined;
   an illumination device for illuminating the eye to be examined;
   a storage device for storing a correction pattern for correcting a reflected image resulting from ghost light generated in an image pickup optical system during illumination by the illumination device;
   a detection device for detecting an image pickup condition; and
   a correction device for correcting the picked up image,
   wherein
   the image of the eye to be examined is corrected by the correction device using the correction pattern stored in the storage device and the correction pattern is in accordance with a detection output of the detection device.

* * * * *